(12) United States Patent
Frank et al.

(10) Patent No.: US 7,118,591 B2
(45) Date of Patent: Oct. 10, 2006

(54) HEAT TRANSFER PROBE

(75) Inventors: Jeffrey I. Frank, Lincolnshire, IL (US);
Axel J. Rosengart, Chicago, IL (US);
Ken Kasza, Palos Park, IL (US);
Wenhua Yu, Woodridge, IL (US);
Tai-Hsin Chien, Darien, IL (US); Jeff Franklin, Woodridge, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 10/827,114

(22) Filed: Apr. 19, 2004

(65) Prior Publication Data

US 2005/0090881 A1    Apr. 28, 2005

Related U.S. Application Data

(60) Provisional application No. 60/463,490, filed on Apr. 17, 2003.

(51) Int. Cl.
*A61F 7/00* (2006.01)
(52) U.S. Cl. .................................. 607/105; 606/28
(58) Field of Classification Search ............ 606/21–31; 607/101–105, 113; 62/93, 118
See application file for complete search history.

(56) References Cited

U.S. PATENT DOCUMENTS

| | | | |
|---|---|---|---|
| 5,281,215 A * | 1/1994 | Milder | 606/20 |
| 5,833,688 A * | 11/1998 | Sieben et al. | 606/41 |
| 6,126,684 A | 10/2000 | Gobin et al. | 607/113 |
| 6,179,831 B1 * | 1/2001 | Bliweis | 606/21 |
| 6,270,493 B1 * | 8/2001 | Lalonde et al. | 606/23 |
| 6,312,452 B1 * | 11/2001 | Dobak et al. | 607/105 |
| 6,500,172 B1 | 12/2002 | Panescu et al. | 606/31 |
| 6,533,804 B1 | 3/2003 | Dobak, III et al. | 607/105 |
| 6,547,811 B1 | 4/2003 | Becker et al. | 105/607 |
| 6,679,906 B1 * | 1/2004 | Hammack et al. | 607/105 |

OTHER PUBLICATIONS

"Computer codes: COMMIX-1AR/P," Reactor Analysis and Engineering, http://www.rae.anl.cov/codes/commix, printed on Apr. 15, 2003.

* cited by examiner

*Primary Examiner*—Michael Peffley
(74) *Attorney, Agent, or Firm*—Michael C. Barrett; Joan Pennington

(57) ABSTRACT

Apparatuses, systems, methods, and computer code for, among other things, monitoring the health of samples such as the brain while providing local cooling or heating. A representative device is a heat transfer probe, which includes an inner channel, a tip, a concentric outer channel, a first temperature sensor, and a second temperature sensor. The inner channel is configured to transport working fluid from an inner inlet to an inner outlet. The tip is configured to receive at least a portion of the working fluid from the inner outlet. The concentric outer channel is configured to transport the working fluid from the inner outlet to an outer outlet. The first temperature sensor is coupled to the tip, and the second temperature sensor spaced apart from the first temperature sensor.

7 Claims, 16 Drawing Sheets

| The cooling capacity of the brain cooling device | | | | | | | | |
|---|---|---|---|---|---|---|---|---|
| Water Properties @ 30C | | | | | | | | |
| ρ | Cp | μ | K | | | | | |
| (kg/m3) | (J/kg-K) | (Pa-s) | (W/m-K) | | | | | |
| 996 | 4180 | 0.000797 | 0.617 | | | | | |
| | | | Coolant inlet temperature (C)= | 25 | 25 | 20 | 20 | |
| | | | Coolant outlet temperature (C)= | 37 | 30 | 37 | 30 | |
| | | | Flow rate (mL/min)= | 170 | 170 | 170 | 170 | |
| | | | Maximum cooling capacity (W)=m*Cp*(Tout-Tin)= | 141.55 | 58.98 | 200.53 | 117.96 | |
| Brain Properties @ 30C | | | | | | | | |
| ρ | Cp | μ | K | | | | | |
| (kg/m3) | (J/kg-K) | (Pa-s) | (W/m-K) | | | | | |
| 1080 | 3850 | | 0.5 | | | | | |
| | | | Temperature drop (C)= | 5 | 5 | 5 | 5 | |

| Cooling time (s)= | 300 | 600 | 900 | 1200 |
|---|---|---|---|---|
| Brain radius (m)= | 0.055 | 0.055 | 0.055 | 0.055 |
| Brain volume (m3)= | 0.000697 | 0.000697 | 0.000697 | 0.000697 |
| Brain mass (kg)= | 0.752663 | 0.752663 | 0.752663 | 0.752663 |
| Required cooling capacity (W)=m*Cp*DT= | 48.30 | 24.15 | 16.10 | 12.07 |
| | | Flow rate (mL/min) | Water (gram) | |
| | | 170 | 50 | |

Calorimetric Experiments

| Time (minute) | Tip Temperature (C) | Calorimeter temperature (C) |
|---|---|---|
| | | To (C) = 23.3 |
| 1 | 10.4 | 23.3 |
| 2 | 10.2 | 23.0 |
| 3 | 9.7 | 22.5 |
| 4 | 9.6 | 21.9 |
| 5 | 9.2 | 21.2 |
| 6 | 9.1 | 20.5 |
| 7 | 8.7 | 19.7 |
| 8 | 8.5 | 19.0 |
| 9 | 8.2 | 18.3 |
| 10 | 8.0 | 17.8 |
| | | Tf (C) = 16.1 |
| | Cooling capacity (W)=m*Cp*DT= | 2.508 |

HEAT TRANSFER PROBE

This application claims priority to, and incorporates by reference, U.S. Provisional Patent Application Ser. No. 60/463,490 which was filed Apr. 17, 2003.

STATEMENT AS TO RIGHTS TO INVENTIONS MADE UNDER FEDERALLY-SPONSORED RESEARCH AND DEVELOPMENT

Aspects of this invention were made with government support of the U.S. Department of Energy, contract no. W-31-109-ENG-38. The government may have certain rights in this invention.

BACKGROUND OF THE INVENTION

1. Field of the Invention

The present invention relates generally to medical devices. More particularly, it concerns a medical probe that can be used to induce localized cooling of tissue, including the brain and other tissue or organs. The localized cooling can reduce local cell death and swelling.

2. Description of Related Art

Traumatic events such as stroke, head trauma, car accidents, falls, etc. may cause localized swelling of tissues and/or organs (e.g., swelling of the brain). Swelling causes increased pressure and blood flow and decreases the ability of affected cells to dissipate heat. It is known that lowering the temperature of the affected cells not only alleviates swelling, but also helps to dissipate heat.

Most conventional cooling systems aimed at treating trauma cool globally instead of locally. In response to trauma, a patient may be subjected to an ice bath or slurry. Although effective to a degree, this type of cooling may lead to other serious problems. For instance, global cooling may cause a heart attack or organ failure.

The ability to apply localized cooling reduces or eliminates such problems. U.S. Pat. No. 6,126,684 to Gobin et al. ("the '684 patent), which is incorporated by reference, describes certain techniques to achieve relatively-localized cooling (or heating). The '684 patent describes a catheter that can be positioned to produce hypothermia in a relatively-selective area of the body without cooling the entire body system. By positioning a heat exchange catheter in a body conduit (e.g. an artery), heat can be added to or removed from the body fluid (e.g. blood) to heat or cool a selected body portion (e.g. the brain). The heat exchange catheter includes a shaft, fluid inlet and outlet lumens, and at least one balloon provided in a heat exchange region. The balloon wall provides a barrier between the body fluid (e.g. blood) and a heat exchange fluid. Although exhibiting some utility, the '684 nevertheless suffers from drawbacks. In particular, the degree of localization afforded is not easily controlled. Because the primary cooling mechanism of the '684 patent involves the cooling of, for instance, a supply fluid, it is difficult or impossible to precisely control or truly localize the cooling. Rather, an entire region (e.g. the entire brain) may be significantly cooled. Additionally, the '684 patent does not provide means to effectively monitor the localization of the cooling or quantify the amount of cooling being effected in tissue. Still further, and importantly, if a body fluid is not present, it appears that techniques of the '684 patent may be inapplicable.

U.S. Pat. No. 6,533,804 to Dobak et al. ("the '804 patent), which is incorporated by reference, describes certain techniques for selective organ heating and cooling. Similar in some respects to the '684 patent, the '804 patent describes a catheter that can be used to change the temperature of a fluid, such as blood, by heat transfer. A catheter system has an inlet lumen and an outlet lumen structured and arranged to carry a working fluid having a temperature different from the adjacent blood. Heat exchange between the two fluids may be utilized, in one embodiment, to cool blood. The '804 patent suffers from drawbacks identical or similar to those of the '684 patent.

Referenced shortcomings of conventional methodologies mentioned above are not intended to be exhaustive, but rather are among many that tend to impair the effectiveness of previously known techniques concerning localized cooling for medical applications. Other noteworthy problems may also exist; however, those mentioned here are sufficient to demonstrate that methodology appearing in the art have not been altogether satisfactory and that a significant need exists for the techniques described and claimed in this disclosure. In particular, a significant need exists for technology that would allow users to achieve localized cooling, which may greatly benefit the treatment of patients, and particularly patients exhibiting localized brain swelling.

SUMMARY OF THE INVENTION

Shortcomings of the prior art are reduced or eliminated by the techniques disclosed in this disclosure. These techniques are applicable to a vast number of applications, including but not limited to any application requiring localized cooling.

In one embodiment, the invention involves a heat transfer probe including an inner tube, an outer tube, a tip, and a first temperature sensor. The inner tube has an opening. The outer tube surrounds the inner tube and is configured to receive working fluid from the inner tube through the opening. The tip is adjacent the opening and terminates the inner and outer tubes. The first temperature sensor is coupled to the tip.

In another embodiment, the invention involves a heat transfer probe, which includes an inner channel, a tip, a concentric outer channel, a first temperatures sensor, and a second temperature sensor. The inner channel is configured to transport working fluid from an inner inlet to an inner outlet. The tip is configured to receive at least a portion of the working fluid from the inner outlet. The concentric outer channel is configured to transport the working fluid from the inner outlet to an outer outlet. The first temperature sensor is coupled to the tip, and the second temperature sensor is spaced apart from the first temperature sensor.

In another embodiment, the invention involves a heat transfer probe, which includes an inner tube, an outer tube, a tip, a first temperature sensor, a second temperature sensor, and an isolation member. The inner tube has an opening and includes a first material. The outer tube surrounds the inner tube and includes a second material. It is configured for fluid communication with the inner tube through the opening. The inner and outer tubes define concentric channels. The tip is adjacent the opening, includes a third material having a thermal conductivity different from that of the first or second material, and terminates the inner and outer tubes. The first temperature sensor is coupled to the tip. The second temperature sensor is spaced apart from the tip and the first temperature sensor. The isolation member couples the second temperature sensor to the outer tube.

In another embodiment, the invention involves a system for effecting heat transfer in tissue and includes a heat transfer probe, a source, a pump, and a controller. The probe includes an inner tube having an opening, an outer tube surrounding the inner tube and configured to receive working fluid from the inner tube through the opening, a tip adjacent the opening that terminates the inner and outer tubes, and a temperature sensor coupled to the tip. The source delivers working fluid to the inner tube and receives working fluid from the outer tube. The pump is coupled to the source, and the controller controls the flow of working fluid to effect heating or cooling of tissue adjacent the probe.

In another embodiment, the invention involves a system for cooling and monitoring tissue and includes a probe, a source, a pump, a first temperature sensor, and a second temperature sensor. The probe is adapted to be inserted into tissue and, includes first and second concentric channels. The first and second concentric channels each have an inlet and an outlet. The source of working fluid is in fluid communication with the first and second concentric channels. The pump is operatively associated with the source and probe. The first temperature sensor is mounted to the probe and adapted to monitor the temperature of the tissue engaging the probe. The second temperature sensor is mounted radially from the probe and is adapted to monitor the temperature of the tissue engaging second temperature sensor.

In another embodiment, the invention involves a method. Working fluid is transported from a source through an inner channel of a probe to change a temperature of tissue adjacent the probe. The working fluid is transported through a concentric outer channel of the probe back to the source. A first temperature of the tissue is sensed at a first location using a first temperature sensor coupled to the probe. A second temperature of the tissue is sensed at a second location using a second temperature sensor spaced apart from the first temperature sensor.

In another embodiment, the invention involves a method of heat transfer and monitoring of tissue. A probe is inserted into the tissue, and the probe has concentric passageways and a temperature sensor. A second temperature sensor is inserted into the tissue at a predetermined distance from the probe. Working fluid is directed through the probe, and the temperature sensed by the first temperature sensor is compared to the temperature sensed by the second temperature sensor.

In another embodiment, the invention involves computer readable media comprising instructions for: obtaining a first temperature of tissue sensed by a first temperature sensor coupled to a heat transfer probe; obtaining a second temperature of the tissue sensed by a second temperature sensor spaced apart from the first temperature sensor; comparing the first and second temperatures; and calculating a thermal transport property of the tissue.

As used herein, "heat transfer" refers to any transfer of thermal energy and in preferred embodiments refers to heating and/or cooling. "Tube" should not be interpreted to connote a particular shape. In particular, "tube" may refer not only to a cylindrically shaped object, but also to objects that are rectangular or any other shape. "Working fluid" simply denotes any fluid that can be transported through a probe, and in preferred embodiments includes cooling or heating fluids. "Working fluid" is not limited to phase characteristics of the fluid. For example, "working fluid" can describe single phase or multi-phase phase change fluids, such as but not limited to commercially available refrigerants. As used herein, "a" and "an" shall not be interpreted as meaning "one" unless the context of the invention necessarily and absolutely requires such interpretation. As used herein, "couple" is not limited to mechanical connections and can include indirect connections with one or more intervening structures.

Other features and associated advantages will become apparent with reference to the following detailed description of specific non-limiting embodiments in connection with the accompanying drawings.

BRIEF DESCRIPTION OF THE DRAWINGS

The following drawings form part of the present disclosure and are included to demonstrate certain aspects of the disclosed technology. That technology may be better understood by reference to one or more of these drawings in combination with the detailed description of specific embodiments.

FIGS. 10 and 10-1 is a table showing cooling capacity in accordance with embodiments of the invention.

DESCRIPTION OF ILLUSTRATIVE EMBODIMENTS

Techniques and probes disclosed here are advantageous at least in that they can provide local cooling of samples such as tissues or organs and can allow for monitoring. The monitoring can be used to quantify the health of tissue in terms of changes or absolute values of local heat transfer characteristics.

Figure 1:
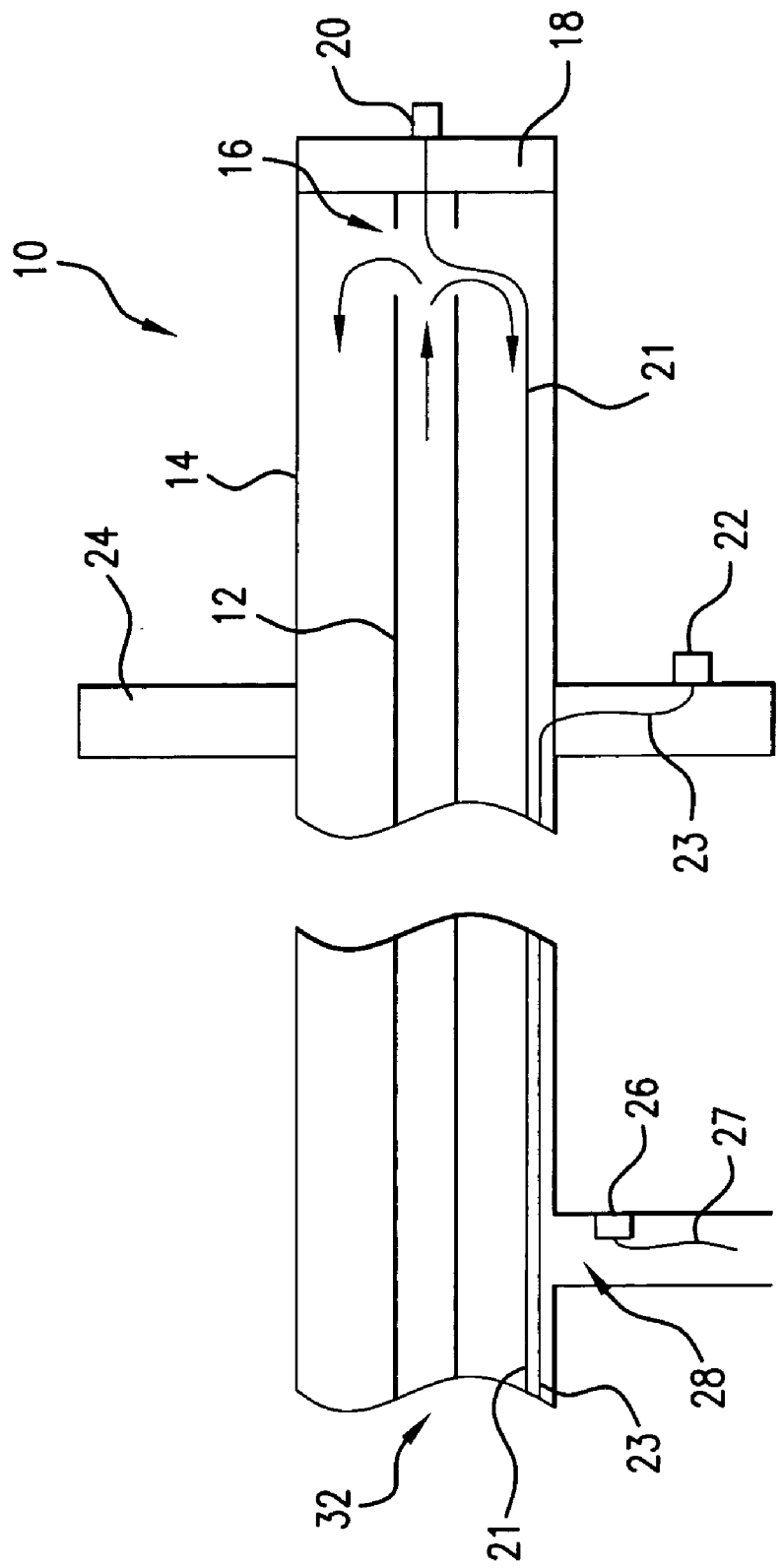
FIG. 1 is an exemplary schematic of a heat transfer probe, in accordance with embodiments of the invention.

FIG. 1 is an exemplary schematic diagram of a heat transfer probe according to embodiments of the invention.

Heat transfer probe 10 includes an inner tube 12 having an opening 16, which receives fluid from an inlet 32. An outer tube 14 surrounds inner tube 12, and outer tube 14 receives fluid from inner tube 12 through opening 16, which is illustrated by the flow arrows of FIG. 1. Tip 18 is adjacent opening 16 and terminates both inner tube 12 and outer tube 14. A first temperature sensor 20 is coupled to tip 18. A second temperature sensor 22 is spaced apart from first temperature sensor 20. An isolation member 24 couples second temperature sensor 22 to outer tube 14. A third temperature sensor 26 is coupled to outlet 28 of outer tube 14.

In one embodiment, inner tube 12 and outer tube 14 may define concentric inner and outer channels respectively, although other arrangements suitable for maintaining fluid flow can be used as well. Inner tube 12 and outer tube 14 can be constructed from any of a number of different materials and have a number of different absolute or relative sizes.

In one embodiment, inner tube 12 and outer tube 14 can be made of the same material, while tip 18 can be made of a different material. In another embodiment, all may be made of the same (or different) material. In one embodiment, the materials of inner tube 12 and outer tube 14 may have a different thermal conductivity than the material of tip 18. In this way, one can control the cooling (or heating) abilities of tip 18 relative to the inner tube 12 and outer tube 14. In one embodiment, inner tube 12 and outer tube 14 may be made from 304 stainless steel tubing commercially available from MCMASTER-CARR. In this embodiment, inner tube 12 may be 19-gauge 304-stainless steel tubing having an outer diameter of 0.042 inches, a wall of 0.0035 inches, an inner diameter of 0.035 inches, a maximum PSI at 72° F. of 2000, and a temperature range of −425 to 600° F. In this embodiment, outer tube 14 may be 12-gauge 304-stainless steel tubing having an outer diameter of 0.109 inches, a wall of 0.0070 inches, an inner diameter of 0.095 inches, a maximum PSI at 72° F. of 2000, and a temperature range of −425 to 600° F.

Opening 16 of inner tube 12 can be any type of opening sufficient to allow fluid to pass through inner tube 12 to outer tube 14. In one embodiment, opening 16 is simply a pair of holes in the outer wall of inner tube 12.

As discussed above, tip 18 can be of the same or different material as inner tube 12 or outer tube 14. Tip 18 is adjacent opening 16, which allows fluid from inner tube 12 (and outer tube 14) to effect a temperature change at and around tip 18. This temperature change, in turn, may effect a temperature change in tissue, or any other material, placed outside the probe in proximity to tip 18. In other words, the temperature of tip 18 may change due to fluid exiting opening 16 and flowing in inner tube 12 and outer tube 14. The temperature of tip 18 can, in turn, be used to cool (or heat) a material placed in its proximity. Of course, it will be understood that the temperature of the entire probe itself may also affect the temperature of a material placed in proximity—tip 18 may not be solely responsible for cooling or heating the material.

In the illustrated embodiment, first temperature sensor 20 is directly connected to tip 18, but in other embodiments, an indirect connection may be used. For instance, first temperature sensor 20 may be connected to a component, which is directly or indirectly connected to tip 18. In another embodiment, first temperature sensor 20 may be connected to outer tube 14, which is, in turn, connected to tip 18. First temperature sensor 20 can be a thermocouple device, although any other type of sensor suitable for measuring temperature may be used as well. In FIG. 1, first temperature sensor 20 is associated with wire 21, although wireless devices and other connection means are contemplated by this disclosure.

Second temperature sensor 22 is spaced apart from first temperature sensor 20. In one embodiment, the spacing is fixed. In other embodiments, the spacing may vary. In either embodiment, the spacing may be pre-determined or readily ascertainable so that thermal calculations depending on a comparison of different temperature readings between the two sensors may be achieved with known boundary conditions. In the illustrated embodiment, second temperature sensor 22 is radially spaced from first temperature sensor 20, in the sense that second temperature sensor 22 is spaced apart from an imaginary line running the length of probe 10. Like first temperature sensor 20, second temperature sensor 22 can be a thermocouple device or another type of sensor. Shown in FIG. 1 is wire 23 serving second temperature sensor 22.

Isolation member 24 couples second temperature sensor 22 to outer tube 14. In one embodiment, isolation member 24 may simply be a disk of material that wraps about outer tube 14. Isolation member 24 may contribute to a degree of thermal isolation between first temperature sensor 20 and second temperature sensor 22.

Third temperature sensor 26 is also spaced apart from first temperature sensor 20. In the illustrated embodiment, third temperature sensor 26 is coupled to outlet 28 of outer tube 14. Like first temperature sensor 20 and second temperature sensor 22, third temperature sensor 26 may be a thermocouple device or another type of sensor. Shown in FIG. 1 is wire 27 serving third temperature sensor 26.

Figure 2:
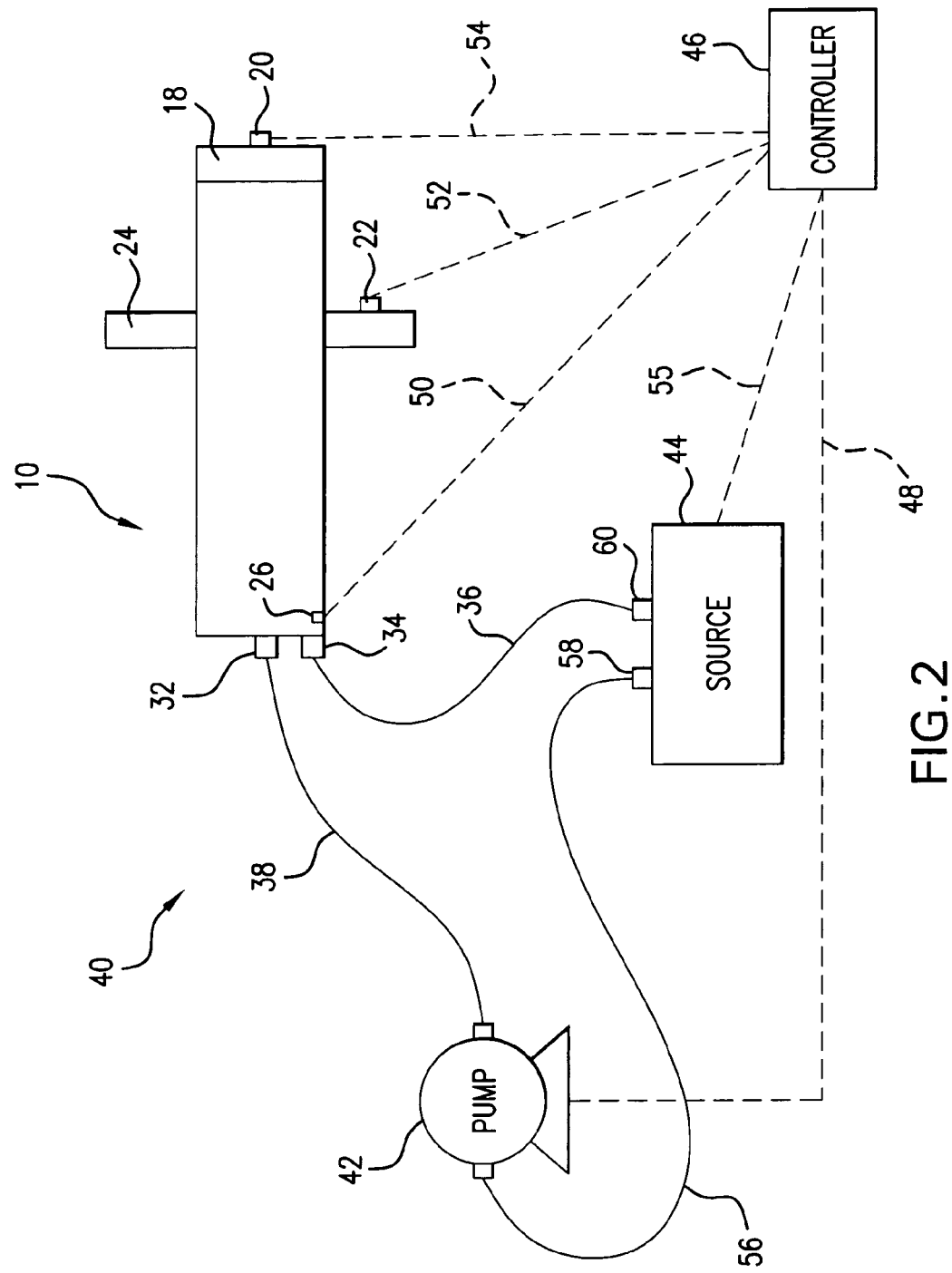
FIG. 2 is an exemplary schematic of a system for heat transfer and/or monitoring tissue, in accordance with embodiments of the invention.
Figure 3:
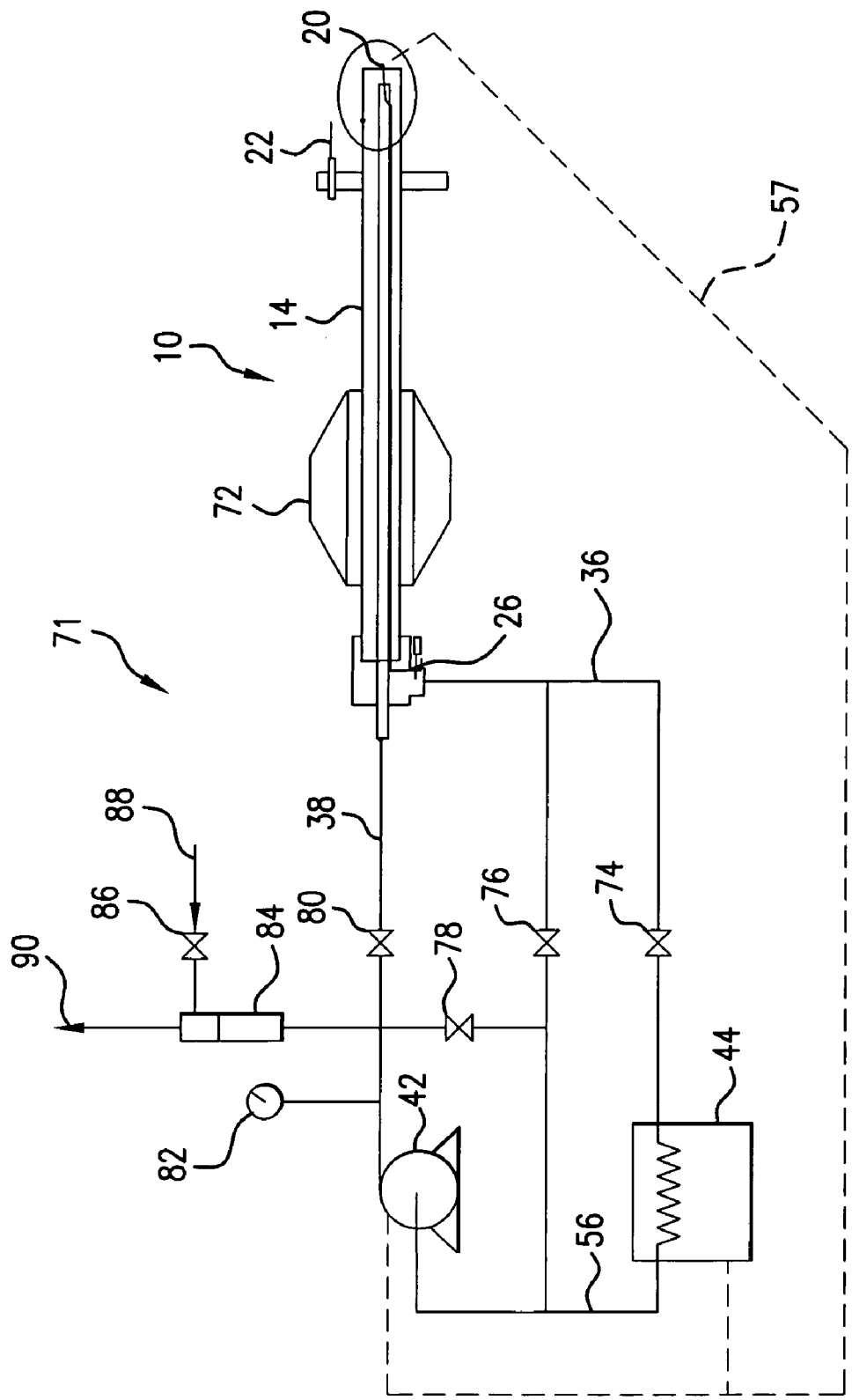
FIG. 3 is an exemplary schematic of another system for heat transfer and/or monitoring tissue, in accordance with embodiments of the invention.

In one embodiment, probe 10 of FIG. 1 operates as follows. Cooling (or heating) fluid from a source, described in relation to FIGS. 2 and 3, is transported through an inlet 32 into inner channel defined by inner tube 12. The working fluid acts to cool (or heat) tissue, or another sample, adjacent probe 10. In one embodiment, the tissue may be brain tissue that has undergone trauma, and the cooling may both reduce swelling and dissipate heat. The working fluid exits opening 16 and enters an outer channel defined by outer tube 14. From there, the working fluid may be transported back to the source. Using first temperature sensor 20, a first temperature of tissue (or other sample) is sensed at a first location. Using second temperature sensor 22, a second temperature of the tissue (or other sample) is sensed at a second location. The distance and/or relative orientation between the first and second positions may be known so as to allow one to calculate a host of thermal properties of the tissue (or other sample) according to equations known in the art according to the known boundary conditions. In one embodiment, a thermal property may be keyed to the relative health of a tissue sample. For instance, a thermal property may indicate whether the tissue is alive, dead, or the proximity to either of these two extremes. The keying of thermal properties to health may be done via a lookup table or the like generated by studying the thermal properties of samples of known health.

FIG. 2 is an exemplary schematic of a system for heat transfer and/or monitoring tissue, in accordance with embodiments of the invention.

System 40 includes probe 10 including elements described in relation to FIG. 1. Probe 10 of FIG. 2 includes inlet 32, which feeds inner tube 12 of FIG. 1 and outlet 34, which receives from outer tube 14 of FIG. 1. System 40 also includes a source 44, which can be a source of working fluid held within. Source 44 includes an inlet 60 (fed by tubing 36) and an outlet 58 (fed by tubing 56). Inlet 60 is coupled to outlet 34 of probe 10. Outlet 58 is coupled to pump 42. Pump 42 delivers fluid, via tubing 38, to inlet 32 of probe 10. Controller 46 can serve a variety of tasks and may be coupled to one or more of temperature sensors 20, 22, and 26, and pump 42.

Outlet 34 of FIG. 2 is drawn as a generic outlet and may, in practice, be designed in accordance with outlet 28 that is illustrated in FIG. 1. Similarly, inlet 32 of FIG. 2 may be implemented in a number of ways and, for instance, may be located at a different location about probe 10. In one embodiment, inlet 32 and outlet 34 are simply openings to probe 10 designed to minimize or eliminate any leakage.

Source 44 can be any type of container suitable for holding fluid. In one embodiment source 44 is a source of working fluid held within. Inlet 60 and outlet 58 can be any opening to source 44 that minimizes or eliminates leakage. In one embodiment, source 44 may be a container akin to a commercially available cooler or chiller.

Tubing 36, 56, and 38 can be any type of tubing commercially available and sufficient to transport fluid. In one embodiment, medical-type tubing may be used. In another embodiment, commercially available COLE PALMER MASTERFLEX® L/S® tubing may be used.

Pump 42 can be any pump suitable for transporting fluid from source 44 to probe 10. In one embodiment, a commercially-available COLE PALMER EW-77914-00 MASTERFLEX® L/S® high-pressure pump may be used.

Controller 46 may be coupled to one or more of temperature sensors 20, 22, and 26, pump 42, and source 44 (and, in other embodiments, a pressure gauge or other instrumentation) and can serve a variety of tasks. In one embodiment, controller 46 may control the flow of fluid via pump 42 to effect cooling of tissue placed adjacent probe 10. In one embodiment, controller 46 may receive feedback from any one or more of temperature sensors 20, 22, or 26 (or other instrumentation) so that the flow of fluid, via pump 42 and/or source 44, may be adaptively controlled based on one or more temperature readings. For example, temperature sensor 20, 22, and/or 26 may sense a temperature that is transmitted to controller 46, which then signals pump 42 and/or source 44 to increase or decrease a rate of fluid flow so that a particular temperature change may be effected. Connections 50, 52, 54, 55, and 48 are shown in FIG. 2 as dashed lines to indicate that the connections may be hardwired, wireless, networked, or made through any other technique known in the art. In one embodiment, controller 46 may be a computer such as a PC, although any computing device sufficient to receive and transmit signals may suffice.

FIG. 2 operates as described with relation to FIG. 1, with the addition that controller 46 may be used as described above. In particular, it may be used to adaptively control the fluid flow through probe 10, based on one or more sensed temperatures or other readings, such as pressure.

FIG. 3 is an exemplary schematic of another system for heat transfer and/or monitoring tissue, in accordance with embodiments of the invention.

System 71 of FIG. 3 shares several elements with the system shown in FIG. 2, and the description given for FIG. 2 therefore applies. FIG. 3 additionally shows a probe holder 72 coupled to outer tube 14. Probe holder 72 may facilitate holding the probe during use and can be designed ergonomically as desired. Dashed line 57 illustrates that first temperature sensor 20 may be linked via wires, wirelessly, networked, or the like through an optional controller (not shown in FIG. 3) to, for example, source 44 (here, shown as a chiller), pump 42, or other equipment. In one embodiment, dashed line 57 may also extend to pressure gauge 82. System 71 includes pressure gauge 82 and valves 74, 76, 78, 80, and 86, which assist in flow management of fluid into and out of probe 10. In one embodiment, valves 86, 78, 76, and 74 may be ball valves commercially available from SWAGELOK INSTRUMENTS, although other valves may be used as well. In one embodiment, valve 80 may be a commercially available NUPRO S SERIES metering valve. Arrow 88 indicates nitrogen/air in, and arrow 90 indicates pressure relief. Element 84 indicates a cooling liquid interface chamber with a pressurization gap that can be used to set the pressure of the circulating coolant, which may be important if the coolant is a refrigerant.

FIG. 3 generally operates as described in relation to FIG. 1 with some additional considerations arising from the illustrated manifold. In one embodiment, working fluid 0.9 wt % saline water may be pumped through metering valve 80 into an inlet of probe 10 (e.g., see element 32 of FIG. 6). The flow rate may be controlled by adjusting valves 80 and 78. Out of an inner channel defined by inner tube 12, the working fluid flows into an outer channel defined by outer tube 14 and tip 18, which may be inserted into the brain. This may bring the local brain temperature down to a range of 25–37° C., although any other temperature ranges are contemplated. After exchanging heat with the brain, the working fluid then goes back to source 44 (e.g., a chiller), which, together with valves 76 and 74, controls the fluid temperature and therefore the cooling speed about 2–5° C. in 5–20 minutes, although other cooling speeds may be readily achieved. Temperature sensors 20, 22, and 26 (e.g., thermocouples) and pressure gauge 82 may provide system information and the base for temperature adjustment.

Figure 4:
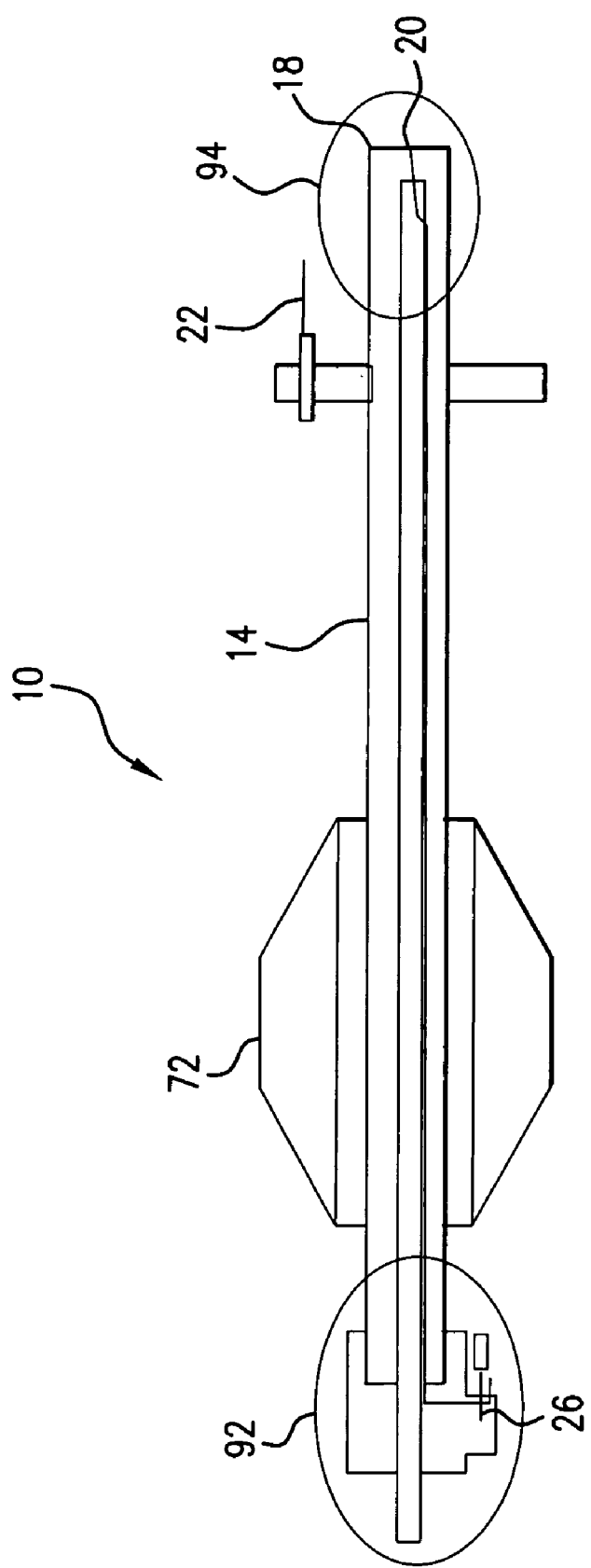
FIG. 4 is an exemplary engineering schematic of another heat transfer probe, in accordance with embodiments of the invention.

FIG. 4 is an exemplary engineering schematic of another heat transfer probe, in accordance with embodiments of the invention.

Probe 10 of FIG. 4 is a exploded view of the probe in FIG. 3. Probe holder 72 and temperature sensors 20, 22, and 26 can be seen more clearly. Although by no means limited to these values, in one embodiment, second temperature sensor 22 lies 6 mm above (with respect to the perspective of FIG. 4) outer tube 14 and 0.5 inches back from the end of tip 18 (i.e. the far end of the probe). In this embodiment, probe holder 72 may be 3 inches back from the end of tip 18.

Figure 5:
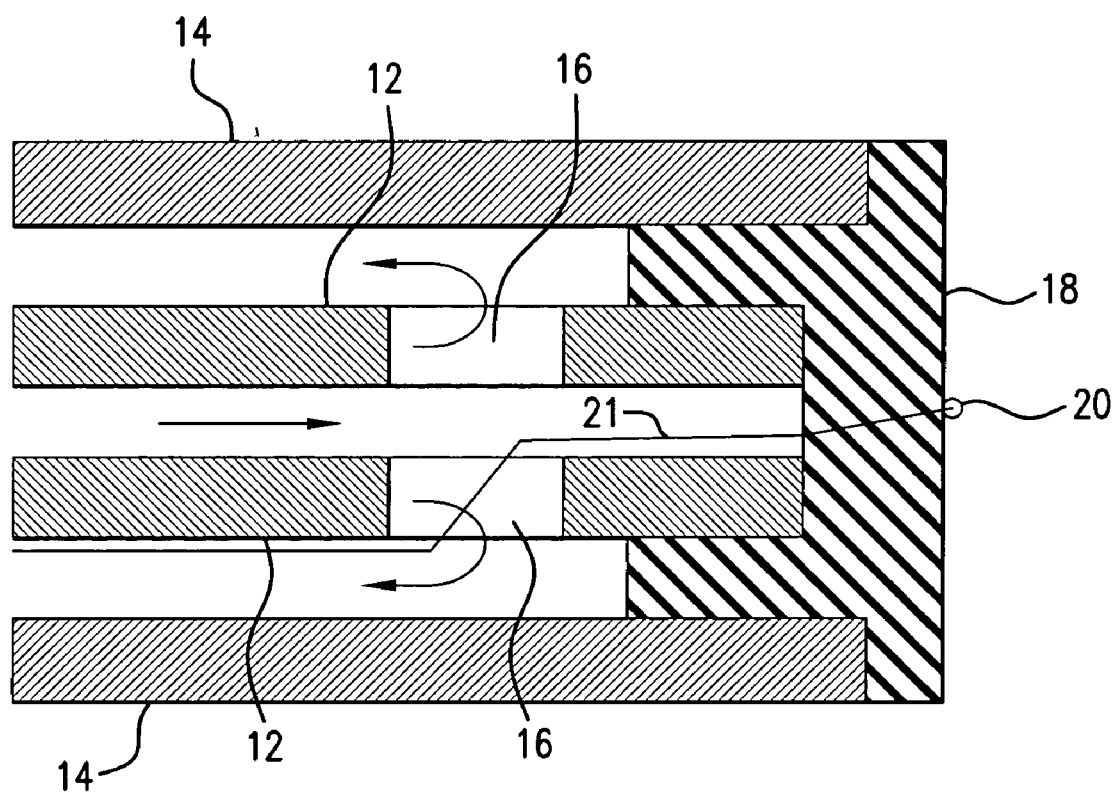
FIG. 5 is an exemplary engineering schematic of a portion of the heat transfer probe of FIG. 4, in accordance with embodiments of the invention.
Figure 6:
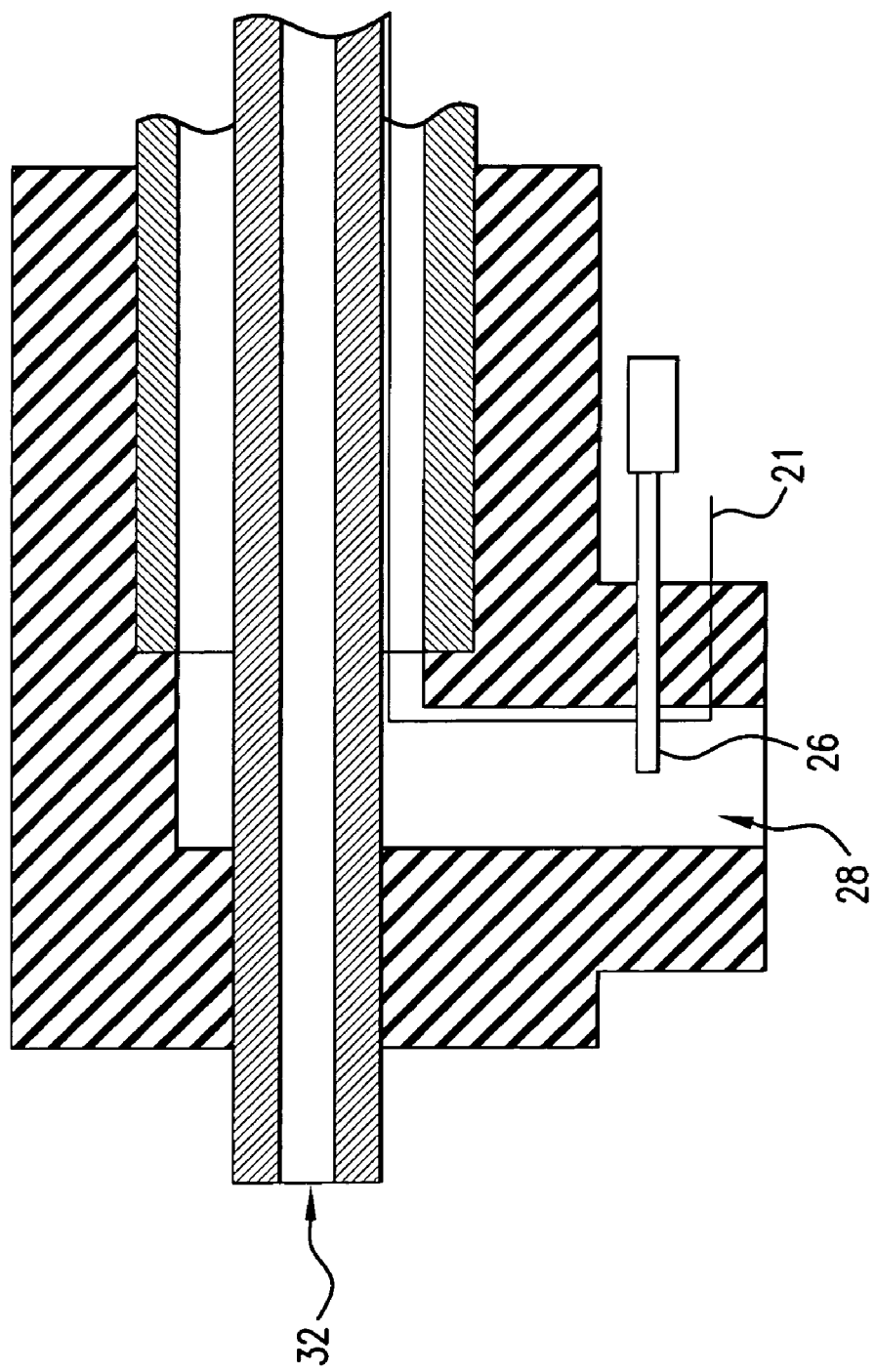
FIG. 6 is an exemplary engineering schematic of another portion of the heat transfer probe of FIG. 4, in accordance with embodiments of the invention.

Areas indicated by circles 94 and 92 in FIG. 4 are shown in FIGS. 5 and 6 respectively.

FIG. 5 is an exemplary engineering schematic of portion 94 of the heat transfer probe of FIG. 4, in accordance with embodiments of the invention.

The description given with respect to FIG. 1 and the other figures applies to FIG. 5, which more clearly shows the tip-end of an exemplary probe.

FIG. 6 is an exemplary engineering schematic of portion 92 of the heat transfer probe of FIG. 4, in accordance with embodiments of the invention.

The description given with respect to FIG. 1 and the other figures applies to FIG. 6, which more clearly shows the outlet-end of an exemplary probe. Also shown is an indication where a probe inlet 32 may be located.

Figure 7:
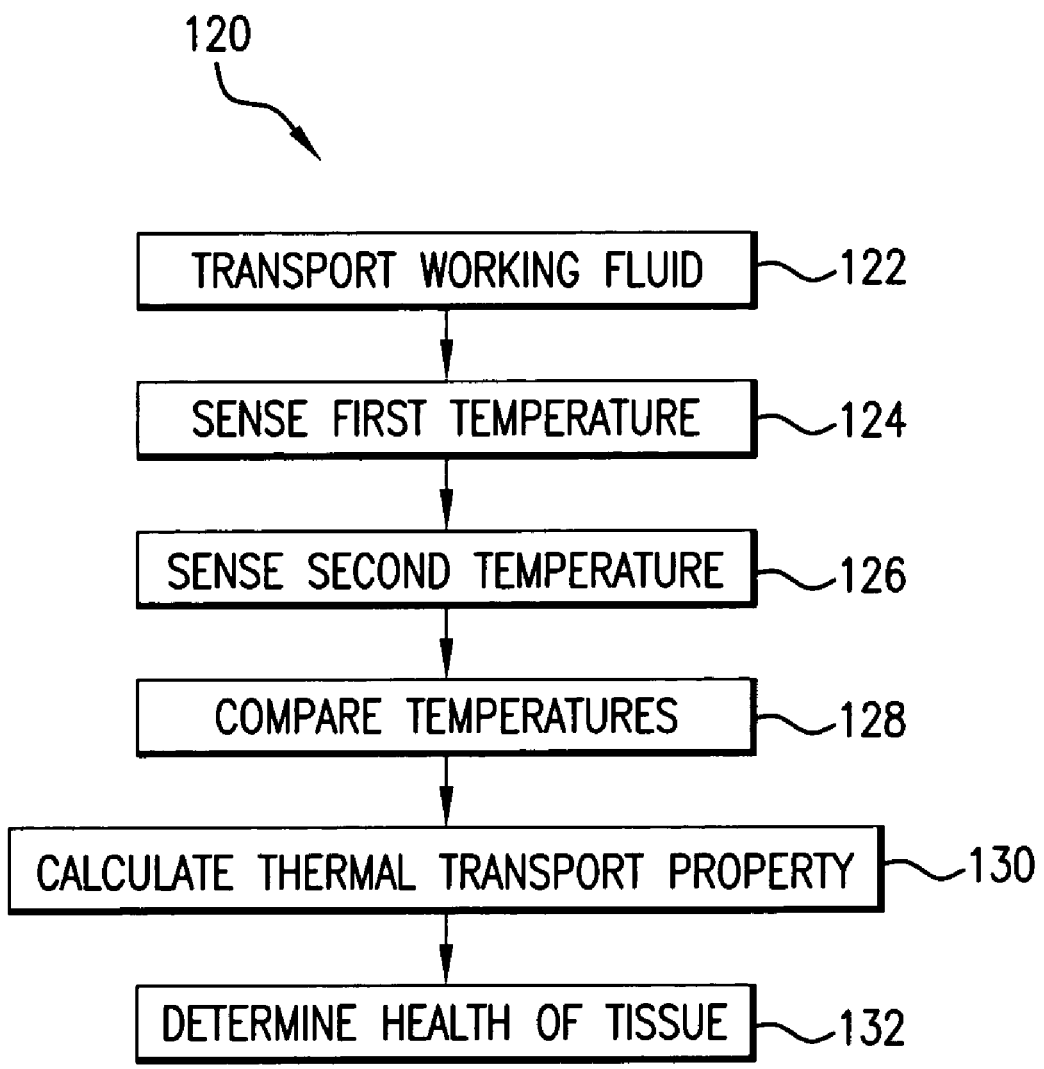
FIG. 7 is an exemplary flow chart of a method in accordance with embodiments of the invention.

FIG. 7 is an exemplary flow chart of a method 120 in accordance with embodiments of the invention.

In step 122, working fluid is transported. In a representative embodiment, the transporting is from source 44 to a probe 10 and back to source 44. In step 124, a first temperature of tissue, or other sample, is sensed using first temperature sensor 20. In step 126, a second temperature of the tissue, or other sample, is sensed using second temperature sensor 22. In a representative embodiment, temperature sensor 20 and second temperature sensor 22 are spaced apart in a known relation. For instance, they may be separated by a fixed, known distance. In step 128, the first and second temperatures are compared and, based on that comparison, a thermal transport property of the tissue, or other sample is calculated in step 130. The thermal transport property may be calculated by mathematical methods well known in the art, given that the two temperatures and their spatial relation set up boundary conditions for a number of mathematical equations that yield a variety of thermal properties. For instance, one may solve an inverse heat transfer problem.

In step 132, a health of the tissue (assuming the sample is tissue) can be determined based on the calculated thermal property. For instance, a certain range of values for a thermal property may correspond to dead tissue while a different range may correspond to living tissue. The ranges may be established by running test cases on tissues known to be dead and alive. Likewise, other ranges may indicate tissues of varying degrees of health. Look-up tables or the like may be utilized to quickly inform the user, upon taking temperature readings, the relative health of tissue.

In different embodiments, steps of method 120 may be implemented in software. For instance, software may be utilized to store the first and second temperatures, compare those temperatures, calculate one or more thermal properties by solving heat equations (and/or their inverses) known in the art given the known boundary conditions of the setup, and determine the health of tissue samples using a lookup table or the like. Such software may be stored on any computer readable media such as but not limited to floppy disk, hard disk, compact disk, DVD, tape, flash memory, firmware running on an ASIC, or any other storage means.

Figure 8:
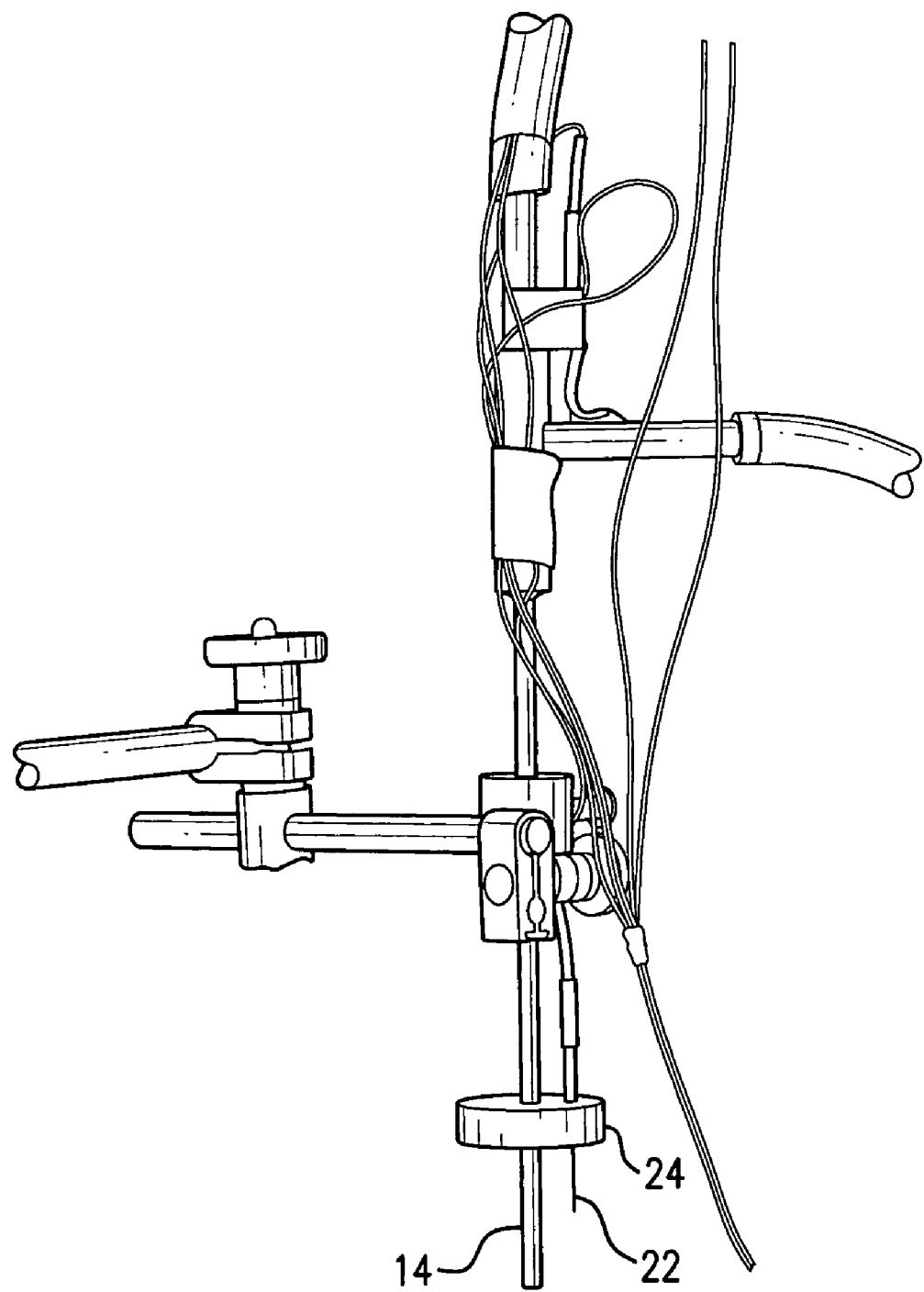
FIG. 8 is a photograph showing an exemplary heat transfer probe in accordance with embodiments of the invention.

FIG. 8 is a photograph showing an exemplary heat transfer probe in accordance with embodiments of the invention. Isolation member 24, second temperature sensor 22, and outer tube 14 are labeled to provide context and perspective for the reader.

Figure 9:
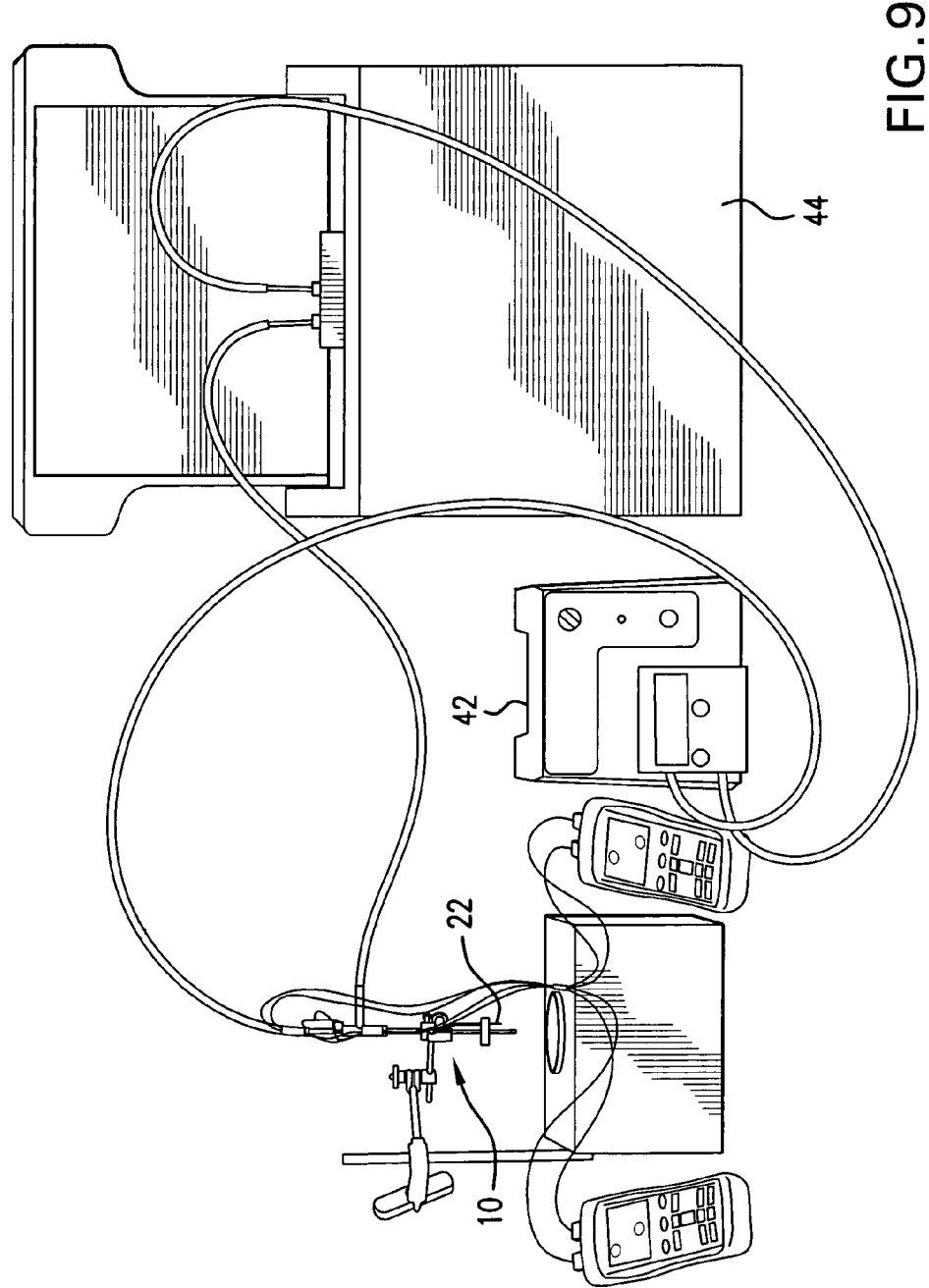
FIG. 9 is a photograph showing an exemplary system for heat transfer and/or monitoring in accordance with embodiments of the invention.

FIG. 9 is a photograph showing an exemplary system for heat transfer and/or monitoring in accordance with embodiments of the invention. Source 44, pump 42, and probe 10 are labeled to provide context and perspective for the reader. Shown in FIG. 9 are two digital recording thermocouple devices that may be used to record temperature data from the probe. The thermocouples used on the probe in the photo are very fine hypodermic gauge devices, which may be selected for fast time response, very low heat capacitance, minimal conduction losses away from the measurement tip, and (in the case of a remote thermocouple such as a thermocouple-implemented second temperature sensor 22) for easy insertion into tissue.

With the benefit of the present disclosure, those having skill in the art will comprehend that techniques claimed herein and described above may be modified and applied to a number of additional, different applications, achieving the same or a similar result. The claims attached hereto cover all such modifications that fall within the scope and spirit of this disclosure.

For example, unless the claims explicitly provide limits, it will be understood that sizes and/or materials of components may be varied as desired. In embodiments in which components are to be inserted into living beings, materials must be designed to be biocompatible. It will also be understood that additional temperature sensors may be placed at various locations on and about probe 10. For instance, one may set up temperature sensors so as to provide convenient mathematical boundary conditions for solving a particular thermodynamic equation. In one embodiment, additional temperature sensors may be placed near inlet 32 and within the inner or outer channels of probe 10.

The following examples are included to demonstrate specific embodiments of this disclosure. It should be appreciated by those of skill in the art that the techniques disclosed in the examples that follow represent techniques discovered by the inventors to function well in the practice of the invention, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the invention. No recitation of temperature ranges, times, etc. should be imported as limitations into the claims, unless the claims explicitly so-require.

EXAMPLES

Objectives

Objectives of techniques of this disclosure include, but are not limited to, the development of a heat exchanger cooling probe that can be used to induce localized cooling of surrounding tissue and monitor changes in tissue health resulting from cell death or deterioration due to insufficient oxygen. This may provide new medical treatment protocols.

The following premises may guide aspects of the invention:

a) inducing targeted hypothermia (cooling) can reduce local cell death and reduce tissue swelling in the brain, other organs, and tissues;

b) cooling characteristics of live and dead tissue are significantly different due to changes in tissue heat transfer characteristics; and c) the literature suggests a few degrees of cooling is cell-protective General Features of Tissue Cooling Probe An exemplary cooling probe developed by the inventors has the following general features:

a) Miniature tube-in-tube heat exchanger b) Designed to operate with very stable/uniform adjustable probe surface temperature when imbedded in tissue c) Can operate with a variety of coolants d) Immersion cooled length is up to 125 mm e) Probe OD is 2.4 mm (can be made much smaller)

f) Instrumented with thermocouples for probe control and monitoring tissue temperature g) Probe when used with heat transfer model and operation procedures can be used to monitor tissue health Exemplary cooling system equipment developed by the inventors includes: an ice bath cooling chest, a 1 gallon coolant ice bath reservoir fitted with a small screened strainer bottle which allows pumping of chilled water by a variable speed high pressure tubing pump into the supply side of the cooling probe without being plugged with ice particles, and a return flow line from the cooling probe which returns warmed coolant back to the ice bath coolant reservoir. The coolant can be chilled water, saline water (or other fluids with other freezing point depressants) for lower operation temperature or other coolants involving phase change in the probe active tip region imbedded in tissue. The probe can also be fitted with a feedback temperature controller/chiller.

The wall thickness of the outer tube of the cooling probe was made of ultra-thin stainless steel metal to reduce thermal resistance between the coolant and the tissue on the outside of the probe to improve cooling effectiveness. The probe outer tube could also be made of other materials of higher thermal conductivity to further reduce thermal resistance or by flexible low friction material to also improve ease of insertion. Towards the same purpose, the flow velocity in the annular gap between the outer and inner coolant supply tube is designed to be very large to increase convective heat transfer between the coolant and the inner surface of the outer tube.

In-addition, to further improve probe performance relative to:

a) cooling effectiveness,
b) facilitating interpretation/modeling of the cooling data,
c) obtaining high quality data on thermal transport properties of tissue, and
d) allowing monitoring of tissue health via changes in transport properties, the flow rate of the coolant delivered to the imbedded probe tip was designed to far exceed that needed to cool the surrounding tissue. And, the flow capacity of the tubing pump and the gap between the inner and outer probe tubes was chosen to achieve these objectives. These features of the design also ensure that the probe immersed zone has a uniform wall temperature that remains essentially constant with time, which in the probe/data modeling section described later may be important to achieving good data.

A calorimeter may be used to make simulated tissue cooling measurements of probe cooling effectiveness. A small, highly-insulated bottle containing water simulates the thermal capacitance of a small region of tissue surrounding the probe tip. Data from such a calorimeter is discussed below.

Cooling Tests with the Cooling Probe

The cooling probe was tested in a calorimeter to evaluate cooling effectiveness before using for animal testing. The calorimeter and animal cooling data from these tests is discussed in this example.

Calorimeter Tests

The calorimeter device to make simulated tissue cooling measurements included a small plastic bottle containing 50 grams of water housed in a highly insulated box, which was allowed to come to thermal equilibrium before probe insertion. The calorimeter was used to simulate the thermal capacitance of a small region of tissue surrounding the probe tip. A sample of the resulting data is discussed below.

A very simplified heat balance calculation shows that the probe has enough cooling capacity to lower brain temperature 5° C. in 5–10 minutes when it is supplied pumped coolant at the flow rate of 170 mL/min (see FIG. 10). This calculation for the conditions presented showed a cooling capacity of 2.5 watts for a 1-in. immersed length.

Figure 11:
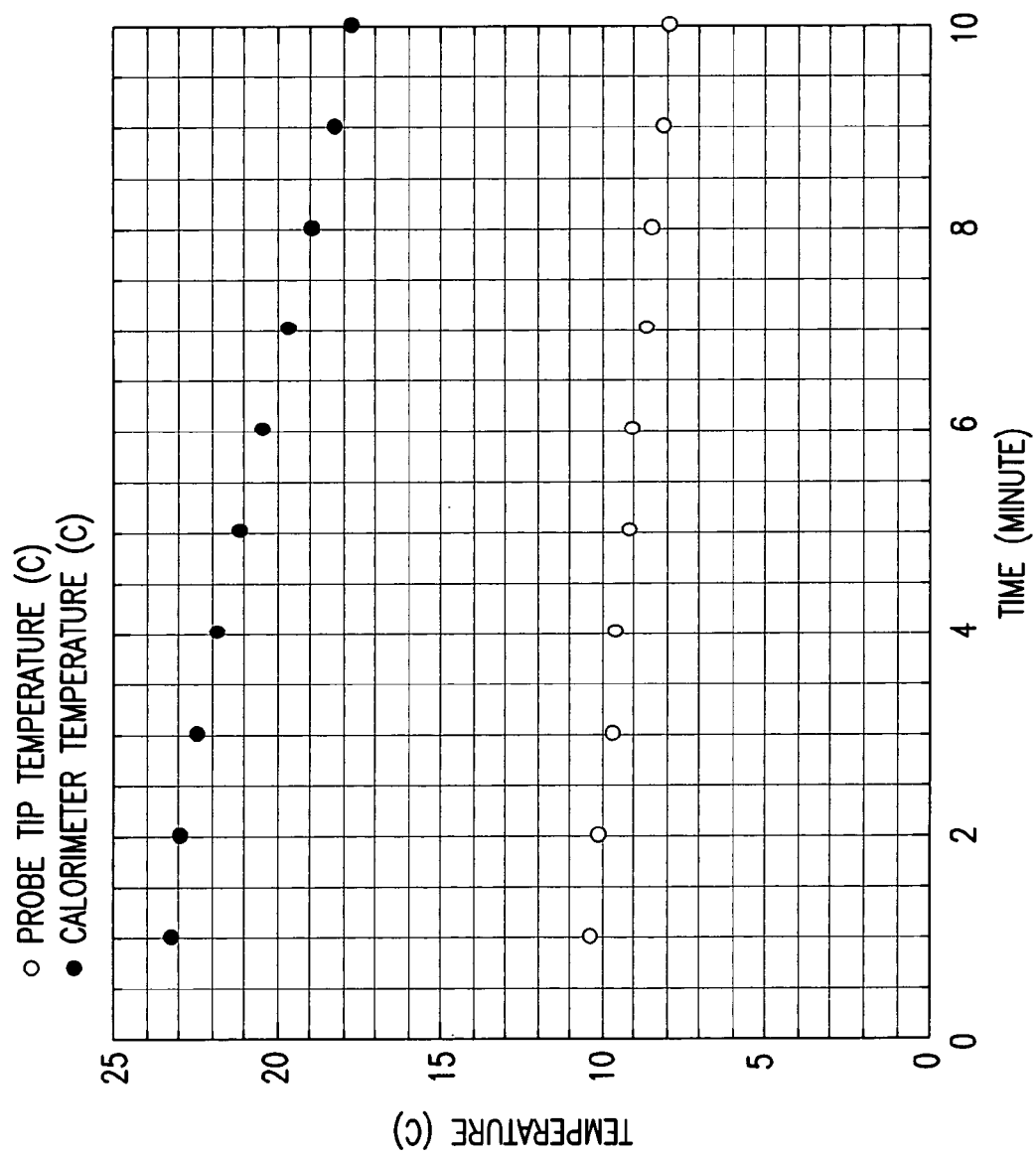
FIG. 11 is a graph showing the temperature change of a probe and water in a calorimeter experiment in accordance with embodiments of the invention.

To further quantify the heat transfer characteristics of the probe, experiments were conducted with the calorimeter. The probe supplied with circulating cooling water at 0° C. was submerged in the calorimeter water initially at room temperature, and the temperatures of the probe and calorimeter water were recorded as a function of time. It can be seen from FIG. 11 that the temperature of the calorimeter drops 5.5° C. within 10 minutes, which shows that probe can locally cool animal brain tissue, which is comprised of a high percentage of water.

Animal Tests

The cooling probe was inserted in live brain tissue to study cooling effectiveness and to measure tissue thermal transport properties. In the live animal tests, the brain is perfused by blood flow and cell metabolism is functioning. The cooling probe was also inserted into dead brain tissue (no blood flow or cell metabolism ), which was removed from the animal to allow study of cooling effectiveness and measure transport properties, which allows, by comparison with data from live tissue, the determination of the difference in cooling and thermal transport characteristics of the two states of tissue. In a later section, a thermal model for these two states will be presented.

Modeling of Probe Cooling/Animal Data

Any number of heat transfer models, using thermodynamic equations known in the art may be utilized with the techniques of this disclosure. The inventors have developed at least two heat transfer models for predicting cooling probe behavior and analyzing tissue and probe temperature data, although neither the claims nor this disclosure is limited to those alone. Utilizing heat models allow one to obtain information on the thermal transport properties of tissue.

One suitable model is a closed form simplified solution of the heat conduction equation summarized below as Case A and the other, Case B, is based on a commercially available multi-dimensional geometry heat transfer and fluid flow finite difference computer code called COMMIX, which allows for modeling regions having an internal heat source or sink. COMMIX is available from the Radiation Safety Information Computational Center of Oak Ridge National Laboratory and, at the time of this disclosure, could be visited at the following web address: http://epicws.epm.ornl.gov. Other multi-dimensional geometry heat transfer and fluid finite difference or finite element algorithms may be used equally well, and the particular use COMMIX itself does not offer any unique advantages in this regard.

In Cases A and B, the modeling assumes the probe is operated in the transient cooling mode with the probe cooled down before insertion into the tissue and then inserted quickly to the desired depth in the tissue. Other modes of operation are also possible and may be utilized with this disclosure. While quickly inserting the probe into the tissue, the temperature data is recorded from the probe wall thermocouple (see, e.g. first temperature sensor 20 in the figures) and the remote thermocouple located a known distance radially outward from the wall (see, e.g., second temperature sensor 22 in the figures).

Modeling of Probe Cooling

Case (A)—Closed Form Solution of Heat Conduction Equation

Considerations:

a) Infinite region bounded internally by the circular cylinder probe r=a
b) Initial temperature $T_i$; Constant wall temperature $T_a$, at r=a for t>0.
c) Alpha is the thermal diffusivity of tissue
d) Simplified for small values of the time $$T = T_i + (T_a - T_i)erfc\frac{r-a}{2\sqrt{\alpha t}}\left\{\frac{a^{1/2}}{r^{1/2}} + \frac{(r-a)(\alpha t)^{1/2}}{4a^{1/2}r^{3/2}}i + \frac{(9a^2 - 2ar - 7r^2)\alpha t}{32a^{3/2}r^{1/2}}i^2 + ...\right\}$$

Case (B) Computer Finite Difference Solution of Heat Conduction Equation with Internal Heat Source in Cylindrical Coordinates (Using COMMIX Code)

Considerations:

a) Tissue internal heat source parameter "q" represents combined influences of perfusion and metabolism b) "q"=0 models dead tissue c) value of "q">0 is measure of tissue health By focusing the modeling analysis on predicting the transient temperature response of the remote thermocouple (see, e.g., second temperature sensor 22 in the figures) in the early time interval after insertion, the uncertainties associated with:

(a) significant thermal exchange at larger times between the probe and the global tissue geometry, and (b) the thermal interactions with the ambient thermal conditions beyond the brain need not be analyzed because these thermal disturbances have not had time to diffuse into the targeted cooling zone. Only the thermal response of the tissue immediately surrounding the probe need be considered. Furthermore, by designing the probe so that the outer wall in contact with the tissue is uniform and nearly constant in temperature, the boundary conditions for the heat transfer models are significantly simplified.

In making predictions with the Case A or B models one solves the inverse heat transfer problem. The transient temperature response of the remote thermocouple imbedded in the tissue (see, e.g., second temperature sensor 22 in the figures) is known, and one may repeatedly guess at the thermal transport properties until one calculates/predicts the temperature response that agrees with the measured data.

When dealing with live tissue, the Case B numerical computer model may be used, and it contains an internal heat source/sink term called "q," which may be used to represent live tissue perfusion and metabolism as a lumped heat generation term.

Figure 12:
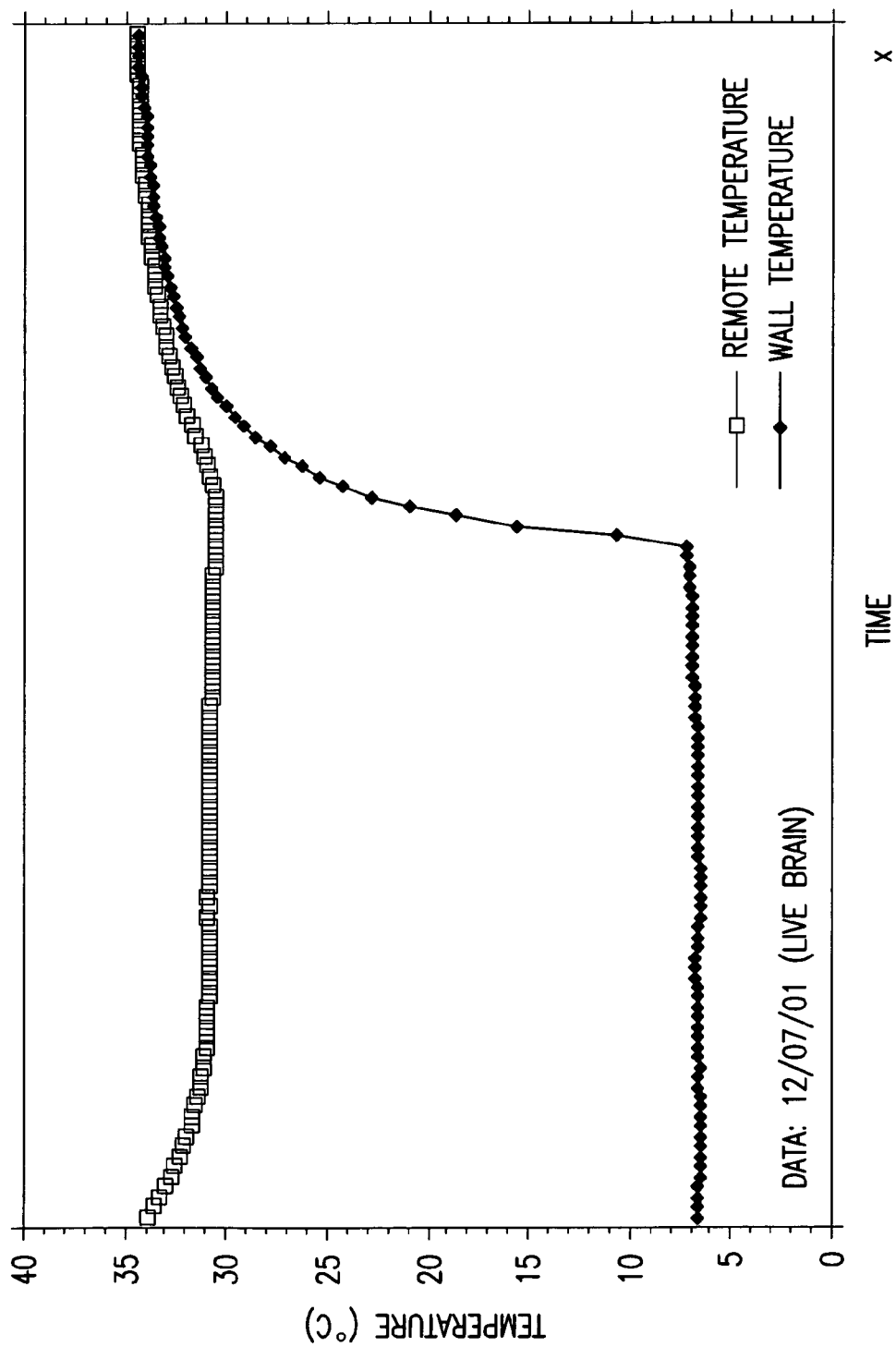
FIG. 12 is a graph showing the transient temperature response of live brain tissue in accordance with embodiments of the invention.

FIG. 12 shows the temperature data from the probe wall and remote thermocouples for a live brain test. Indeed, the probe wall temperature is constant upon insertion, and the tissue at the remote location drops several degrees quickly and then stabilizes. At a much larger time, the coolant to the probe was turned off, and the probe and remote temperatures rise back up to normal brain temperature. The data as previously discussed is only analyzed in the first minute or so to get the brain tissue thermal characteristics.

Figure 13:
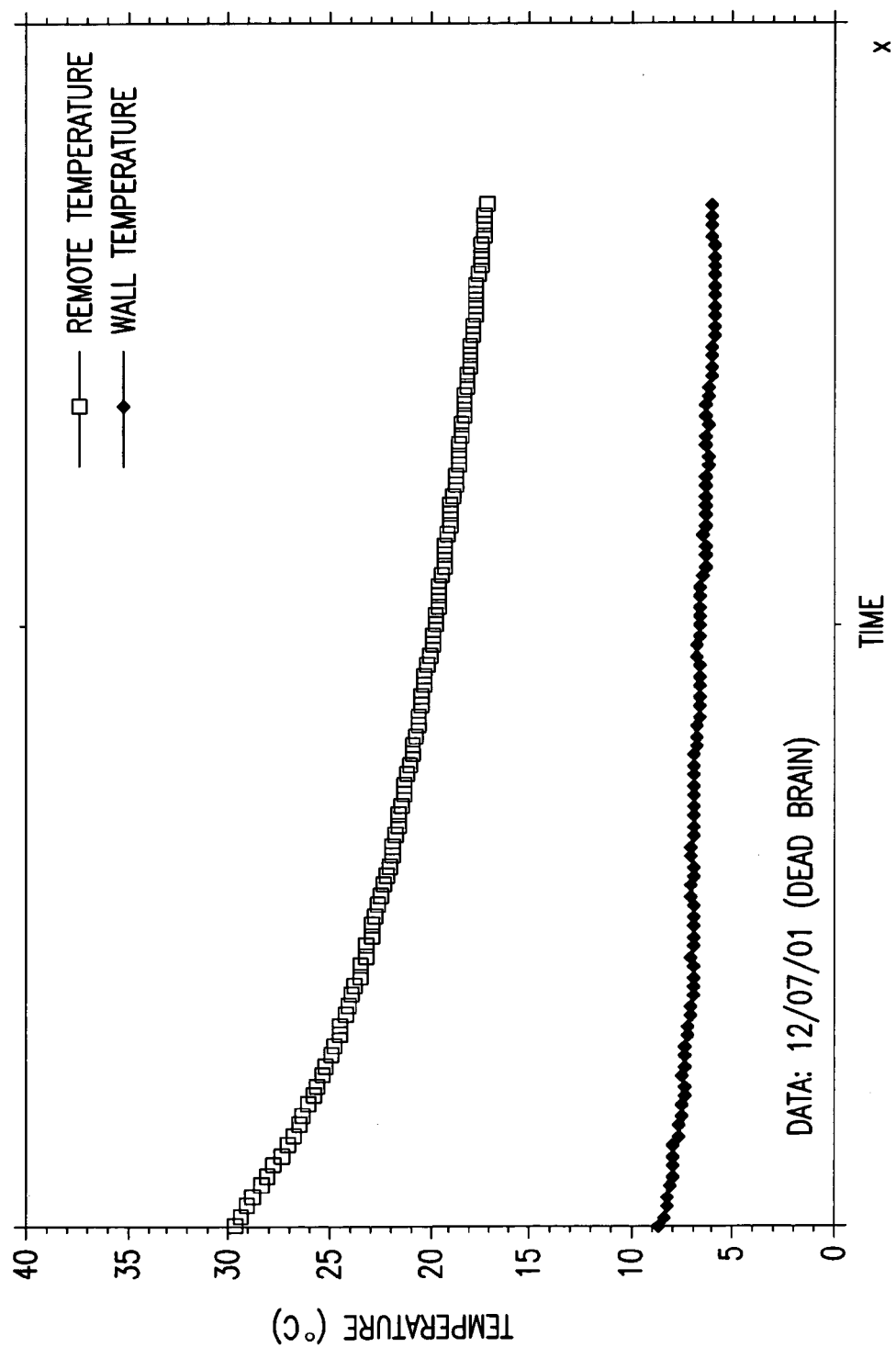
FIG. 13 is a graph showing the transient temperature response of dead brain tissue in accordance with embodiments of the invention.

FIG. 13 shows the temperature data from the probe wall and remote thermocouples for a dead brain test. Again the probe wall temperature is nearly constant upon insertion, and the tissue at the remote location drops several degrees quickly and continues to drop in response to the probe because there is no perfusion or metabolism. The data as previously discussed is only analyzed in the first minute or so to get the brain tissue thermal characteristics.

Figure 14:
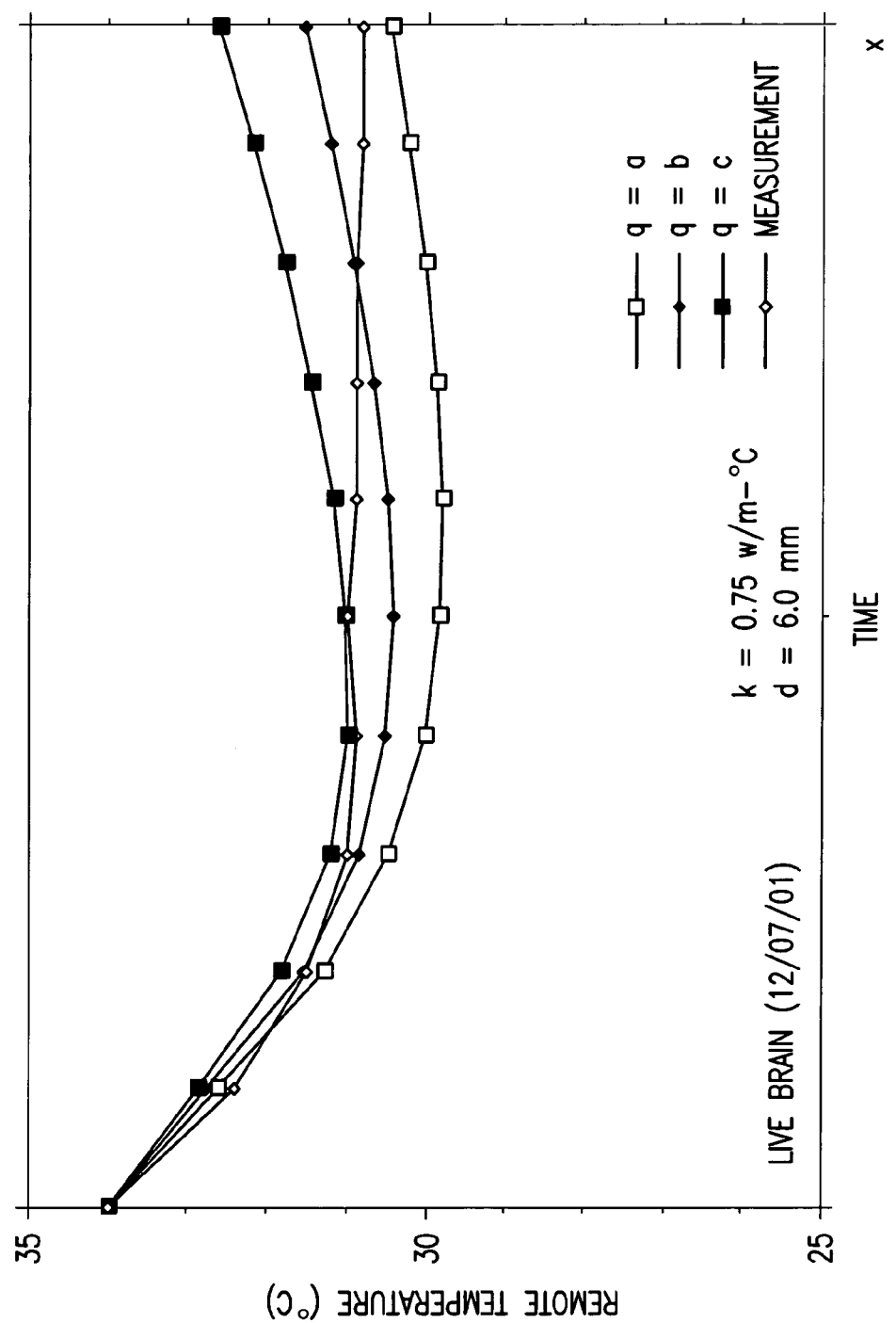
FIG. 14 is a graph showing the transient temperature cooling response for small time and various assumed values "q" of the tissue heat source parameter in accordance with embodiments of the invention.

FIG. 14 shows the predicted small time response of the remote thermocouple (see, e.g., second temperature sensor 22 in the figures) for live brain tissue for three guesses at "q," and the measured transient temperature. A value of "q" equal to 0.05 w/cm$^3$ was found to represent the small time behavior tissue behavior. For additional live tissue test data, a value of "q" close to this value was obtained. As noted earlier, "q" represents in live tissue the influence of perfusion and metabolism. For dead tissue, "q"=0. Hence, by this modeling approach, for a particular probe use, by tracking changes in "q" with time and comparing the value to that from healthy tissue, one can use the probe to monitor tissue health. Relative health states between "living" and "dead" may be readily monitored by creating, for example, look up tables correlating different health states to different thermal properties.

Figure 15:
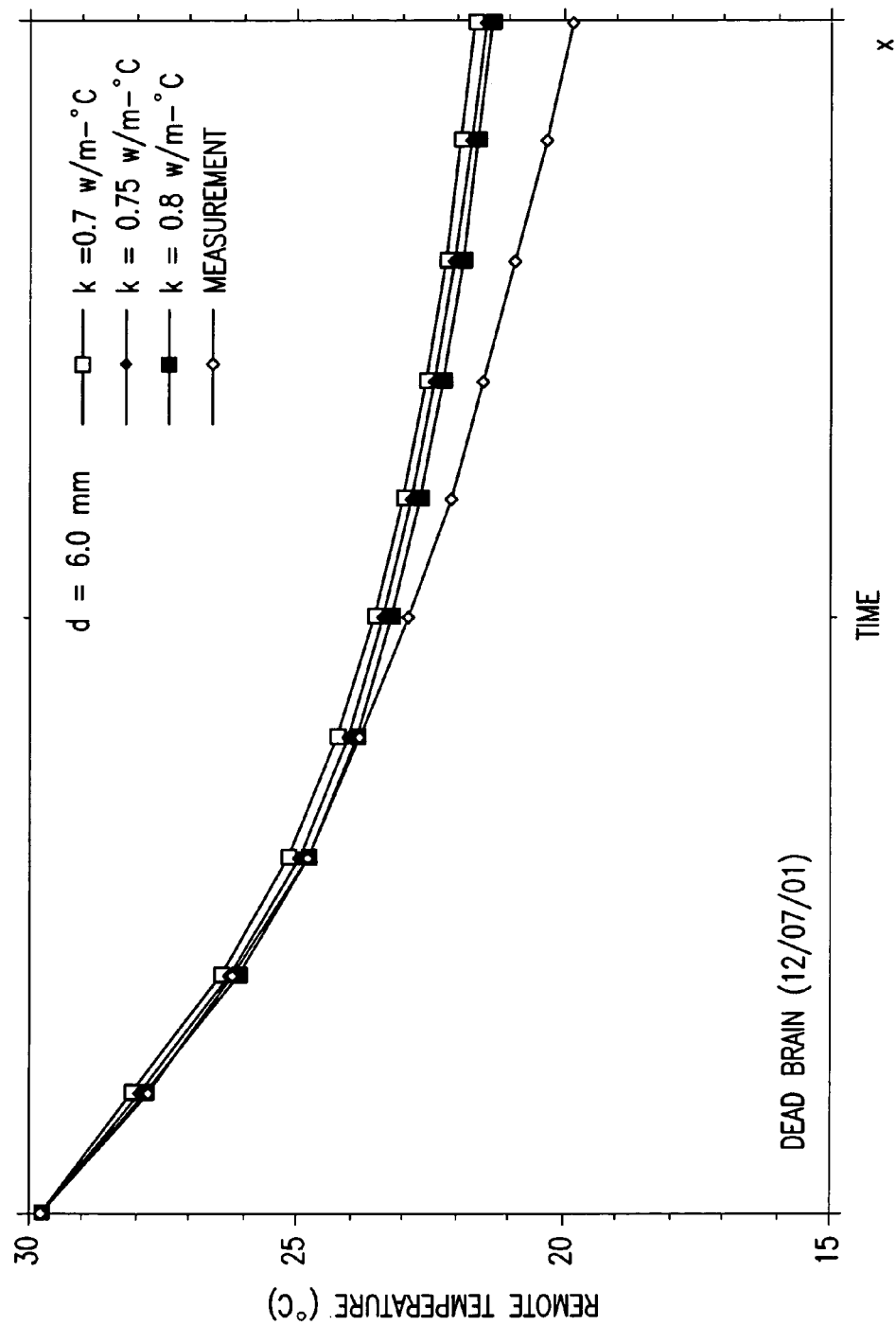
FIG. 15 is a graph showing a comparison between dead brain tissue measured and predicted transient temperature cooling response for small time and various assumed values of thermal conductivity in accordance with embodiments of the invention.

FIG. 15 shows the measured temperature data from the remote thermocouple (see, e.g., second temperature sensor 22 in the figures) for a dead brain test, where there is no perfusion or metabolism, and the predicted response for several values of guessed tissue thermal conductivity. A value of thermal conductivity of about 0.75 w/m-° C. is found to yield a good prediction. The data as previously discussed is only analyzed in the first minute or so to get the brain tissue thermal characteristics. The literature reports scattered values of k in the range 0.4 to 0.85 w/m-° C. for several different types of tissue.

The table below presents results from the model for live and dead brain tissue thermal conductivity for several tests.

| Brain tissue | Tissue initial temperature (° C.) | Probe wall temperature (° C.) | Predicted thermal conductivity (w/m-° C.) |
|---|---|---|---|
| dead | 25.2 | 6.1 | ~0.7 |
| live | 34.0 | 6.7 | ~0.75 |
| dead | 29.8 | 7.0 | ~0.7 |
| live | 34.3 | 5.6 | ~0.8 |
| dead | 25.2 | 5.6 | ~0.75 |
| Cadaver | 23.0 | 5.6 | ~0.8 |

Results and Conclusions Based on Results from Analysis and Modeling

Data on localized cooling of perfused brain (alive) tissue and non perfused (dead) brain after sacrifice were obtained. The probe in both cases had its cooling tip imbedded 1-in. deep into brain tissue, and the temperature of the probe's outer surface and that of brain tissue located radially 7.8 mm away from the probe was measured versus time. At time zero minus a little, the probe was cooled to nominally 5° C. and then inserted into the brain. Upon full insertion, which is taken as time zero, the thermal response of the probe and brain tissue was recorded for up to 15 minutes. The following are some observations:

1) Advantageously to computational modeling, the outer surface temperature of the imbedded probe region remained quite constant after a few seconds of transient adjustment time.

2) For both the perfused and non perfused brain, a significant volume of brain tissue out to the remote thermocouple and certainly to lesser amount beyond the 7.8 mm radius, tissue temperature was seen to drop 3° C. and 9° C. respectively on the order of 10 minutes. All brain tissue locations closer to the cooling probe than the remote thermocouple were at temperature between the remote thermocouple and the wall temperature of 5° C. There is significant cooling locally around the probe and this has therapeutic hypothermia value in reducing tissue swelling and cell death.

3) The data from the perfused alive case when compared with dead brain data is important to an understanding of brain cooling and relating thermal behavior to the diagnostics of the health of brain tissue. For the perfused case, the remote temperature dropped quickly 3° C. and after a few minutes achieved steady state. This results from the fact that blood perfusion into the cooling zone and brain heat generation from metabolism are offsetting the cooling from the probe, and, locally, a state of equilibrium is reached. Because there is such a big difference between the two cases (perfused vs. non perfused), modeling can be used to quantify and separate out the impact of the phenomena on local cooling. Furthermore, because the thermal response of brain tissue is so drastically different for alive and dead brains, one may use the cooling probe not only for therapeutic hypothermia, but also for a host of diagnostic tools for quantifying the progression or growth of brain tissue death or reduced perfusion, among other things. For example, if the cooling probe when initially imbedded into a suspect brain zone suffering from stroke or trauma damage shows only a 3° C. drop in temperature of the brain tissue, but several hours later under the same probe cooling conditions shows a larger drop in remote tissue temperature, one can infer that locally more tissue has died as a result of reduced perfusion and metabolism in the region of interest.

Summary

The cooling probe and systems tested by the inventors have been shown to be capable at least of the following:

a) cooling live tissue 4 to 5° C. in a cylindrical region surrounding the immersed probe length;

b) measuring the thermal conductivity of tissue, alive or dead; and c) diagnosing the health of surrounding tissue by changes in cooling characteristics.

With the benefit of the present disclosure, those having skill in the art will comprehend that techniques claimed herein may be modified and applied to a number of additional, different applications, achieving the same or a similar result. The claims attached hereto cover all such modifications that fall within the scope and spirit of this disclosure. The claims are to be afforded their ordinary and accustomed meaning unless the disclosure provides different, explicit definitions, and the claims are not to be limited by importing limitations from the specification or the examples.

REFERENCES

Each of the following references is hereby incorporated by reference in its entirety:

U.S. Pat. No. 6,547,811
U.S. Pat. No. 6,126,684
U.S. Pat. No. 6,533,804

We claim:

1. A method comprising:

transporting working fluid from a source through an inner channel of a probe to change a temperature of tissue adjacent the probe;

transporting the working fluid through a concentric outer channel of the probe back to the source;

sensing a first temperature of the tissue at a first location using a first temperature sensor coupled to the probe;

sensing a second temperature of the tissue at a second location using a second temperature sensor spaced apart from the first temperature sensor, the difference between the first and second temperatures being used to determine a thermal property of the tissue;

comparing the first and second temperatures; and calculating a thermal transport property of the tissue based on the comparison.

2. The method of claim 1, further comprising determining the health of the tissue based on the thermal transport property.

3. The method of claim 2, determining the health comprising determining whether the tissue is alive or dead.

4. A method comprising:

transporting working fluid from a source through an inner channel of a probe to chance a temperature of tissue adjacent the probe;

transporting the working fluid through a concentric outer channel of the probe back to the source;

sensing a first temperature of the tissue at a first location using a first temperature sensor coupled to the probe;

sensing a second temperature of the tissue at a second location using a second temperature sensor spaced apart from the first temperature sensor, the difference between the first and second temperatures being used to determine a thermal property of the tissue;

comparing the first and second temperatures; and adjusting a flow rate of the working fluid based on the comparison.

5. A media comprising computer-executable instructions for:

obtaining a first temperature of tissue sensed by a first temperature sensor coupled to a heat transfer probe;

obtaining a second temperature of the tissue sensed by a second temperature sensor spaced apart from the first temperature sensor;

comparing the first and second temperatures;

calculating a thermal transport property of the tissue from the comparison of the first and second temperatures; and indicating a health of the tissue based on the thermal transport property.

6. The media of claim 5, the instructions for indicating the health comprising instructions for indicating whether the tissue is alive or dead.

7. A media comprising computer-executable instructions for:

obtaining a first temperature of tissue sensed by a first temperature sensor coupled to a heat transfer probe;

obtaining a second temperature of the tissue sensed by a second temperature sensor spaced apart from the first temperature sensor;

comparing the first and second temperatures;

calculating a thermal transport property of the tissue from the comparison of the first and second temperatures; and providing a signal to a controller used for varying a flow rate of working fluid.

* * * * *